(12) United States Patent
Marshall et al.

(10) Patent No.: US 12,014,329 B2
(45) Date of Patent: *Jun. 18, 2024

(54) PET INSURANCE SYSTEM AND METHOD

(71) Applicant: Trupanion, Inc., Seattle, WA (US)

(72) Inventors: Kerri E. Marshall, Seattle, WA (US);
Darryl Rawlings, Seattle, WA (US);
Kathryn Plowman, Portland, ME (US);
Christopher Cappelletti, Carnation, WA (US)

(73) Assignee: TRUPANION, INC., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/941,483

(22) Filed: Jul. 28, 2020

(65) Prior Publication Data
US 2020/0364667 A1   Nov. 19, 2020

Related U.S. Application Data

(63) Continuation of application No. 16/023,624, filed on Jun. 29, 2018, which is a continuation-in-part of (Continued)

(51) Int. Cl.
   *G06Q 40/08*   (2012.01)
   *G06Q 10/10*   (2023.01)
   (Continued)

(52) U.S. Cl.
   CPC ............. *G06Q 10/10* (2013.01); *G06Q 40/08* (2013.01); *G16H 40/20* (2018.01); *G16H 10/60* (2018.01)

(58) Field of Classification Search
   CPC ...... G06Q 40/08; G06F 19/328; G16H 10/60; G16H 50/70
   See application file for complete search history.

(56) References Cited

U.S. PATENT DOCUMENTS 5,720,502 A   2/1998   Cain
6,117,526 A   9/2000   Marks et al.
(Continued)

FOREIGN PATENT DOCUMENTS

CN    1756477 A    4/2006
CN  101925919 A   12/2010
(Continued)

OTHER PUBLICATIONS

2011 Trupanion set up: pp. 15 to 17 https://mc9ljrfyiceiaeu2gdfotgw0-wpengine.netdna-ssl.com/wp-content/uploads/2019/09/AVImark-Release-Notes-2011.3.6.pdf, 25 pages.
(Continued)

*Primary Examiner* — Reginald R Reyes
(74) *Attorney, Agent, or Firm* — Wilson Sonsini Goodrich & Rosati

(57) ABSTRACT

This disclosure relates to a system and method implemented to facilitate real-time medical coverage for veterinary hospitals. More specifically, the disclosure as a pet medical insurance system pet medical insurance claims system comprising: a backend component implemented on a computer, the backend component comprising a services component; a plug-and-play data integration system connected to a first practice management system in a veterinary practice and the backend component. The plug-and-play data integration system receives data from the first practice management system and maps the data according to the backend system, thereby limiting the data traffic between the backend component and the first practice management system. The plug-and-play data integration system is integratable with a second or more different practice management systems for receiving data that is different from the data from the first practice management system.

12 Claims, 20 Drawing Sheets

Related U.S. Application Data application No. 14/924,606, filed on Oct. 27, 2015, now Pat. No. 10,013,530, which is a continuation-in-part of application No. 14/210,079, filed on Mar. 13, 2014.

(60) Provisional application No. 61/801,404, filed on Mar. 15, 2013.

(51) Int. Cl.
*G16H 40/20* (2018.01)
*G16H 10/60* (2018.01)

(56) References Cited

U.S. PATENT DOCUMENTS

| | | | |
|---|---|---|---|
| 6,966,064 B1 | 11/2005 | Schneidewend et al. | |
| 7,155,405 B2 | 12/2006 | Petrovich | |
| 7,266,770 B2 | 9/2007 | Onbe et al. | |
| D572,717 S | 7/2008 | Loehr et al. | |
| 7,496,583 B2 | 2/2009 | Moore et al. | |
| D605,653 S | 12/2009 | Danton | |
| 7,711,660 B1 * | 5/2010 | Gentile | G06Q 40/08 705/2 |
| 8,341,547 B2 | 12/2012 | Ingman et al. | |
| 8,359,605 B2 | 1/2013 | Ross | |
| D777,737 S | 1/2017 | Marshall et al. | |
| 10,013,530 B2 | 7/2018 | Marshall et al. | |
| 10,255,993 B2 | 4/2019 | Marshall et al. | |
| 10,891,590 B2 | 1/2021 | Marshall et al. | |
| 2002/0099276 A1 | 7/2002 | Schmidt et al. | |
| 2003/0004740 A1 | 1/2003 | Dickey et al. | |
| 2003/0187695 A1 | 10/2003 | Drennan | |
| 2004/0254816 A1 | 12/2004 | Myers | |
| 2005/0060344 A1 | 3/2005 | Pawlick | |
| 2005/0091606 A1 | 4/2005 | Sauermann | |
| 2006/0074724 A1 * | 4/2006 | Schwartz | G06Q 40/08 705/4 |
| 2006/0075724 A1 | 4/2006 | Kammler et al. | |
| 2006/0196436 A1 | 9/2006 | Nichols | |
| 2006/0251775 A1 | 11/2006 | Anderson et al. | |
| 2007/0084099 A1 | 4/2007 | Sarbo et al. | |
| 2007/0203758 A1 * | 8/2007 | Stephens | G06Q 40/08 705/4 |
| 2008/0040157 A1 | 2/2008 | Saunders | |
| 2008/0172617 A1 | 7/2008 | Takeda et al. | |
| 2008/0307339 A1 | 12/2008 | Boro et al. | |
| 2009/0083079 A1 | 3/2009 | Law et al. | |
| 2009/0106678 A1 | 4/2009 | Chase et al. | |
| 2009/0182586 A1 | 7/2009 | Cohane | |
| 2009/0289844 A1 | 11/2009 | Palsgrove et al. | |
| 2009/0300540 A1 | 12/2009 | Russell | |
| 2010/0017234 A1 | 1/2010 | Stephens et al. | |
| 2010/0293487 A1 | 11/2010 | Schoenberg | |
| 2011/0119574 A1 † | 5/2011 | Rogers | |
| 2011/0131507 A1 | 6/2011 | Butcher | |
| 2012/0060105 A1 | 3/2012 | Brown et al. | |
| 2012/0060216 A1 † | 3/2012 | Chaudhri | |
| 2012/0110453 A1 | 5/2012 | Ma et al. | |
| 2012/0265702 A1 | 10/2012 | Maher | |
| 2013/0073366 A1 | 3/2013 | Heath | |
| 2013/0218592 A1 * | 8/2013 | Hashmat | G06F 21/6245 705/3 |
| 2014/0052463 A1 * | 2/2014 | Cashman | G06Q 10/1095 705/2 |
| 2014/0155785 A1 | 6/2014 | Haas | |
| 2014/0278551 A1 | 9/2014 | Marshall et al. | |
| 2016/0364547 A1 | 12/2016 | Love et al. | |
| 2018/0349852 A1 | 12/2018 | Marshall et al. | |
| 2020/0167731 A1 | 5/2020 | Marshall et al. | |

FOREIGN PATENT DOCUMENTS

| | | | |
|---|---|---|---|
| JP | 2002073802 A | 3/2002 | |
| JP | 2002132918 A | 5/2002 | |
| JP | 2004005588 A | 1/2004 | |
| JP | 2004267183 A | 9/2004 | |
| JP | 2006107069 A | 4/2006 | |
| JP | 2010140513 A | 6/2010 | |
| JP | 2013022984 A | 2/2013 | |
| KR | 20070081610 A | 8/2007 | |
| WO | WO-2006036316 A1 | 4/2006 | |
| WO | WO-2014152179 A2 | 9/2014 | |
| WO | WO-2017075207 A1 | 5/2017 | |

OTHER PUBLICATIONS 2012 1st Annual Naphia Conference. Vetenvoy featured presenter. ("1st annual naphia summit_VE Described_Copied for Patent.pdf") 7 pages.

2012 ACT, Sep. 2008 PurinaCare. ("ACT Automated Claims Processing Feb. 2012 Proposal.doc") 9 pages.

Avimark 2011 announcement of offering ("Avimark_2011-Insurance Update.pdf") 1 page.

Avimark, ("Avimark-Release-Notes-2011.3.6.pdf") https://docplayer.net/63752091-Avimark-readme-table-of-contents-please-use-the-bookmark-menu-on-the-left-to-navigate-between-each-project-and-feature-1.html, 21 pages (accessed on Apr. 15, 2020).

Avimark, http://docplayer.net/11571437-Vpi-eclaim-equote-integration.html, 18 pages (accessed on Apr. 15, 2020).

Avimark Insurance and vetenvoy, https://www.petinsurance.com/images/VSSimages/landingPages/Vet_Envoy_AVImark/setup.pdf, 3 pages (accessed on Apr. 15, 2020).

AVImark ReadMe 2011.3.0 Link: https://docplavernet/63752091-Avimark-readme-table-of-contents-please-use-the-bookmark-menu-on-the-left-to-navigate-between-each-project-and-feature-1.html(Year: None).

"AVImark eClaims Instructions v2.0 for Trupanion.pdf", 22 pages (2012).

European search report dated Dec. 9, 2016 for EP Application No. 14770490.

International search report with written opinion dated Nov. 29, 2016 for PCT/US2016/059095.

Notice of allowance dated May 17, 2018 for U.S. Appl. No. 14/924,606.

Notice of allowance dated May 29, 2018 for U.S. Appl. No. 14/924,606.

Notice of allowance dated Nov. 28, 2018 for U.S. Appl. No. 16/115,446.

Office action dated Jan. 18, 2019 for U.S. Appl. No. 14/210,079.

PCT/US2014/27042 International Search Report and Written Opinion dated Oct. 1, 2014.

PracticeOn: https://cdn.website-editor.net/f8ec393e8489444b912f11c22465414a/files/uploaded/Connector%2520v101%2520Insurance%2520Trials%2520Submission%2520Instructions%2520for%2520AVImark.pdf https://cdn.website-editor.net/f8ec393e8489444b912f11c22465414a/files/uploaded/Connector%2520v101%2520Insurance%2520Trials%2520Submission%2520Instructions%2520for%2520AVImark.pdf, 7 pages (2018).

PracticeOn in the market in Canada. https://www.practiceon.com/connector-insurance-support, 2 pages (2019).

Request for Ex Parte Reexamination filed Mar. 2, 2020 (56 pages) for U.S. Appl. No. 90/020,134 by PracticeOn Limited.

Trupanion_Avimark_PracticeOn 2011 Flyer.https://drive.google.com/file/d/1DNh3EVeoUwXaeh3-rfsTlvxdppDXhiHj/view?ts=5e587265 ("Trupanion_Avimark_Vetenvoy Practice Flyer.pdf") 1 page.

U.S. Appl. No. 16/023,624 Notice of Allowance dated Feb. 21, 2020.

U.S. Appl. No. 16/023,624 Notice of Allowance dated Jul. 15, 2020.

U.S. Appl. No. 16/023,624 Notice of Allowance dated May 15, 2020.

U.S. Appl. No. 14/210,079 Final Office Action dated Sep. 5, 2017.

U.S. Appl. No. 14/210,079 Non-Final Office Action dated Dec. 7, 2016.

U.S. Appl. No. 14/210,079 Non-Final Office Action dated Mar. 21, 2018.

(56) References Cited

OTHER PUBLICATIONS

U.S. Appl. No. 14/210,079 Non-Final Office Action dated Sep. 6, 2019.
U.S. Appl. No. 14/210.079 Office Action dated Jun. 10, 2020.
U.S. Appl. No. 14/924,606 Final Office Action dated Jul. 22, 2016.
U.S. Appl. No. 14/924,606 Final Office Action dated Oct. 12, 2017.
U.S. Appl. No. 14/924,606 Non-Final Office Action dated Jan. 12, 2017.
U.S. Appl. No. 14/924,606 Non-Final Office Action dated Mar. 10, 2016.
U.S. Appl. No. 16/023,624 Non-Final Office Action dated Oct. 31, 2019.
U.S. Appl. No. 16/779,338 Office Action dated May 28, 2020.
U.S. Appl. No. 29/449,619 Final Office Action dated Jul. 17, 2015.
U.S. Appl. No. 29/449,619 Non-Final Office Action dated Oct. 3, 2014.
U.S. Appl. No. 29/449,619 Notice of Allowance dated Sep. 13, 2016.
Vetenvoy / Livetime 24/7 Public and Open API, Feb. 12, 2008 ("Vet Envoy Services API v1.50.pdf") http://www.vetenvoy.com/uk/content/vet%20envoy%20services%20api%20v1.50.pdf, 109 pages.
Vetenvoy's architecture, design and workflows. ("VE IT Topology.pdf") 5 pages (accessed on Apr. 15, 2020).
Vetenvoy in the press example, Dec. 2009 http://www.vetenvoy.com/uk/Content/VetEnvoy%20VBJ%20article.pdf, 4 pages.
Vetenvoy publicly shared information, Apr. 2009. https://veterinary-practice.com/article/a-giant-step-towards-the-paperless-office, 7 pages.
Vetenvoy.com information about eclaims, 2009. http://www.vetenvoy.com/, http://www.vetenvoy.com/, 2 pages.
Vetmessenger on 350+ practices 2012/13+ https://vimeopro.com/4act/vetenvoy-messenger-client-software/video/66664634, 1 page.
Vetmessenger on 350+ practices 2012/13+ https://www.dropbox.com/s/pddxa0ecflrcch1/New%20Development%2004.23.2013%20VetMessenger.mp4?dl=0, 1 page.
VetXML Consortium ("vetxml_timeline page.docx") http://www.vetxml.co.uk/en/about-the-consortium/#about-the-consortium, 7 pages (2020).
VPI eClaim & eQuote Integraeon Link: http://docplavernet/11571437-Vpi-eclaim-eauote-integration.html (Year: None).
AVImark, now Covetrus Software Services, AVImark Release Notes 2011.1.7, 75 pages https://softwareservices.covetrus.com/avimark-legacy-release-notes/, 2011.
U.S. Appl. No. 16/023,624 Notice of Allowance dated Oct. 15, 2020.
Wikipedia, https://en.wikipedia.org/w/index.php?title=Plug_and_playoldid=539757675, Plug and Play, Feb. 22, 2013.
Wikipedia, Plug and Play, 1 Page, Feb. 22, 2013, https://en.wikipedia.org/w/index.php?title=Plug_and_play&oldid=539757675.†
AVImark, now Covetrus Software Services, AVImark Release Notes 2011.1.7, 75 Pages, 2011, https://softwareservices.covetrus.com/avimark-legacy-release-notes/.†

\* cited by examiner
† cited by third party

FIG. 3

- trupanion express*
- ☐ Appointments
- ❀ Pets
- ☐ Claims
- ⊙ Certificates
- ⋈ Reports
- ☐ Start New Claim
- ⊞ Offer Certificate
- ✆ 000.733.2670
- ● TRUPANION.COM

— 501

Search by pet name, owner last name, or phone number — 502

Help ⊙

2:00 pm
- Zeus — John & Melissa Stuart — Start Claim
- Waldo — John Oliver — Offer Certificate ⌄
- Sylvester — Theo Munster — Offer Certificate ⌄
- Chunky Brewster — Juliette Pompell — Offer Certificate ⌄
- Toaster — Theo Crabapples — Claim Processed Pay to Client: Paid — 504

2:30 pm
- Hooch — Scott Turner — Offer Certificate ⌄
- Lady — Jim Dear — Offer Certificate ⌄
- Benji — Joe Camp — View Decision Approved — 504
- Carter — Brian Trenton — Offer Certificate ⌄
- Oberlin — Brain Trenton — Start Claim — 503

3:00 pm
- Bear — Shirley Little — Offer Certificate ⌄
- Giada — Beatrice & John Singleton — Offer Certificate ⌄
- Mouse — Delilah Hart — Offer Certificate ⌄
- Lemon — Ida Shaw — Offer Certificate ⌄
- Yarn — Dorothy Goodman — View Decision $850.142 Trupanion Payment
- Fang — Rubeus Hagrid — Offer Certificate ⌄

3:30 pm
- Ricky — Ralph McMann — Certificate Offered — 505
- Rose — Thaddeus Farr — Offer Certificate ⌄
- Ree — Norman Diltz — Offer Certificate ⌄
- Christmas — Bob & Dariene Cook — Offer Certificate ⌄
- Dog — Winifred Dundy — Offer Certificate ⌄
- Elf — Josephine — Offer Certificate ⌄

4:00 pm
- CJ — Albert & Agnes Finkleman — Offer Certificate ⌄
- Vargus — Brian Trenton — Offer Certificate ⌄
- Cheddar — Lucille & Lou — View Decision $150.53 Trupanion Payment
- Viola — Brian Trenton — Start Claim
- Hadley — Brian Trenton — Claim Processed Pay to Client: Ineligible
- Peanut — Walter Depp — View Decision Ineligible

4:30 pm No appointments for this time

| Show ○ All ● Last 30 days | Sort by | Issue Date ▽ | ⇩ |

| | | |
|---|---|---|
| Vargus<br>Brian Trenton<br>Email: briantrenton@test.com | Issued: 12/10/2014 | 21hrs<br>Status: Issued |
| Oberlin<br>Brian Trenton<br>Email: briantrenton@test.com | Issued: 12/10/2014 | 19hrs<br>Status: Issued |
| Sadie<br>Josh Logan<br>Email: joshlogan@test.com | Issued: 12/09/2014 | Status: Expired |
| Swoops<br>Tina & Mark Johnson<br>Email: tinaandmark@test.com | Issued: 12/09/2014 | Status: Expired |
| Liona<br>Stacy May<br>Email: stacymay@test.com | Issued: 12/09/2014 | Status: Expired |
| Hadley<br>Brian Trenton<br>Email: briantrenton@test.com | Issued: 12/09/2014 | Status: Activated |

FIG. 8B

FIG. 11A trupanion express*

Search by pet name, owner last name, or phone number 🔍    Help ⓘ

- 🗓 Appointments
- 🐾 Pets
- 🗂 Claims
- 📍 Certificates
- 📊 Reports
- 📋 Requests [4]
- ☐ Start New Claim
- 🖨 Offer Certificate
- ☏ 000.733.2670
- ⊙ TRUPANION.COM Requests    [Print All Fax Cover Sheets] [Print All Requests] [Batch Upload]

| Overdue | Needed Today | Needed Later | Open | Completed | Expired | Cancelled |
|---|---|---|---|---|---|---|
| ⊙ 2 | 🗓 4 | 🗓 10 | 👁 13 | ☑ 65 | ⊙ 3 | ✕ 10 |

Show ☑ Active ☐ Completed    Group by [Priority]    Sort by [Aging Number] ⬇

∨ Critical Claims [1]

Rocky    [Attach ∨]
[Critical] Dan Smith & Danielle Smith    [Reply]
Status Requested    Full Medical History 06/1/2014 - 01/26/2015
Aging 2 hrs    Labs    Imaging    [Submit ∨]
Created 01/26/2015    • Bloodwork    • Radiographs
Pol# TU0004637827    • Urinalysis    • Ultrasound
Claim# C7489387    • Other. Lorem Ipsum    • MRI
   • Other: Dolor Sitt 💬 1 new    📎 2 attachments    Expand ∨ Urgent Claims [3]

Igor    [Attach ∨]
[URGENT] Richard Sherman    [Reply]
Status Requested    Full Medical History 06/1/2014 - 01/26/2015
Aging 6 hrs    Labs    Imaging    [Submit ∨]
Created 01/26/2015    • Bloodwork    • Radiographs
Pol# TU0004637827    • Urinalysis    • Ultrasound
Claim# C7489387    • Other. Lorem Ipsum    • MRI
   • Other: Dolor Sitt 💬 3 comments    📎 2 attachments    Expand

Igor    [Attach ∨]
[URGENT] Richard Sherman    [Reply]
Status Requested    Radiographs 06/01/2014 - 01/26/2015
Aging New    • Radiographs    [▒ ∨]
Created 01/26/2015
Pol# TU0004637827
Claim# C7489387

💬 0 comments    📎 0 attachments    Expand

∨ Standard Claims [3]

Johnny    [Attach ∨]
[URGENT] Richard Sherman    [Reply]
Status Requested    Full Medical History 06/1/2014 - 01/26/2015

| trupanion express* | Search by pet name, owner last name, or phone number | | | Help ⓘ |
|---|---|---|---|---|
| 🗓 Appointments | 2:00 PM 🐾 Zeus — John & Mellissa Stuart — Start Claim | 🐾 Waldo — John Oliver — Offer Certificate › | 🐾 Sylvester — Theo Musiber — Offer Certificate › | 🐾 Chunky Brewster — Juliette Potpell — Offer Certificate › | 🐾 Toaster — Theo Crabapples — Claim Processed |
| 🐾 Pets | 2:30 PM 🐾 Hooch — Scott Turner — Offer Certificate › | 🐾 Lady — Jim Dear — Offer Certificate › | 🐾 Benji — Joe Camp — View Decision Approved | 🐾 Carter — Brian Trenton — Offer Certificate › | 🐾 Oberlin — Brian Trenton — Start Claim | 🐾 Fang — Rubeus Hagrid — Offer Certificate › |
| 📄 Claims | 3:00 PM 🐾 Bear — Shirley Little — Offer Certificate › | 🐾 Giada — Beatrice & John Singleton — Offer Certificate › | 🐾 Mouse — Dellah Hart — Offer Certificate › | 🐾 Lemon — Ida Shaw — Offer Certificate › | 🐾 Yarn — Dorothy Goodman — View Decision | 🐾 Elf — Josephine — Offer Certificate › |
| 🏅 Certificates | 3:30 PM 🐾 Ricky — Ralph McMann — Certificate Offered | 🐾 Rose — Thaddeus Farr — Offer Certificate › | 🐾 Ree — Norman Ditz — Offer Certificate › | 🐾 Christmas — Bob & Darlance Cook — Offer Certificate › | 🐾 Dog — Winifred Dundy — Offer Certificate › | 🐾 Peanut — Walter Depp — View Decision |
| 📊 Reports | 4:00 PM 🐾 CJ — Albert & Agnes Finkleman — Offer Certificate › | 🐾 Vargus — Brian Trenton — Offer Certificate › | 🐾 Cheddar — Lucile & Lou — View Decision | 🐾 Viola — Brian Trenton — Start Claim | 🐾 Hadley — Brian Trenton — Claim Processed | |
| 📄 Start New Claim 🏅 Offer Certificate ☎ 888.733.2670 🌐 TRUPANION.COM | 4:30 PM No appointments for that time | | | | | |

| | | | | | | | |
|---|---|---|---|---|---|---|---|
| Appointments 2:00 pm | 🐾 Zeus John & Melissa Stuart | 🐾 Waldo John Oliver | 🐾 Chunky Brewster Juliette Pompell | 🐾 Sylvester Theo Munster | | 🐾 Fang Rubeus Hagrid | |
| | Start Claim | Offer Certificate ⌄ | *Claim Decision Available for Nil* | Offer Certificate ⌄ | | Offer Certificate ⌄ | |
| | | | View Decision $42,345.09 Paid | | | | |
| | | | Claim Processed Pay to Client: Paid | | | | |
| 2:30 pm | 🐾 Hooch Scott Turner | 🐾 Lady Jim Dear | | 🐾 Benji Joe Camp | 🐾 Carter Brian Trenton | 🐾 Oberlin Brian Trenton | 🐾 Elf Josephine |
| | Offer Certificate ⌄ | Offer Certificate ⌄ | | View Decision Approved | Offer Certificate ⌄ | Start Claim | Offer Certificate ⌄ |
| 3:00 pm | 🐾 Bear Shirley Little | 🐾 Giada Beatrice & John Singleton | | 🐾 Mouse Delilah Hart | 🐾 Lemon Ida Shaw | 🐾 Yarn Dorothy Goodman | 🐾 Peanut Walter Depp |
| | Offer Certificate ⌄ | Offer Certificate ⌄ | | Offer Certificate ⌄ | Offer Certificate ⌄ | View Decision $8501.42 Trupanion Payment | View Decision Ineligible |
| 3:30 pm | 🐾 Ricky Ralph McMann | 🐾 Rose Thaddeus Farr | | 🐾 Ree Norman Diltz | 🐾 Christmas Bob & Dariene Cook | 🐾 Dog Winifred Dundy | |
| | Certificate Offered | Offer Certificate ⌄ | | Offer Certificate ⌄ | Offer Certificate ⌄ | Offer Certificate ⌄ | |
| 4:00 pm | 🐾 CJ Albert & Agnes Finkleman | 🐾 Vargus Brian Trenton | | 🐾 Cheddar Lucille & Lou | 🐾 Viola Brian Trenton | 🐾 Hadley Brian Trenton | |
| | Offer Certificate ⌄ | Offer Certificate ⌄ | | View Decision $150.53 Trupanion Payment | Start Claim | Claim Processed Pay to Client: Ineligible | |
| 4:30 pm | No appointments for this time | | | | | | | trupanion express*

- Appointments
- Pets
- Claims
- Certificates
- Reports
- Start New Claim
- Offer Certificate
- 000.733.2670
- TRUPANION.COM

PET INSURANCE SYSTEM AND METHOD

PRIORITY CLAIMS/RELATED APPLICATIONS

This application claims priority under 35 U.S.C. § 120 and is a continuation of U.S. patent application Ser. No. 16/023,624, filed on Jun. 29, 2018, now U.S. Pat. No. 10,909,501, and entitled "Pet Insurance System and Method," which claims priority under 35 U.S.C. § 120 and is a continuation in part of U.S. patent application Ser. No. 14/924,606, filed on Oct. 27, 2015, now U.S. Pat. No. 10,013,530, and entitled "Pet Insurance System and Method," which in turn claims priority under 35 U.S.C. § 120 and is a continuation in part of U.S. patent application Ser. No. 14/210,079, filed on Mar. 13, 2014, now U.S. Pat. No. 10,891,590, and entitled "Pet Insurance System and Method," which in turn claims priority to and the benefit under 35 U.S.C. § 119(e) of U.S. Provisional Patent Application Ser. No. 61/801,404, filed on Mar. 15, 2013, and entitled "Pet Insurance System and Method," the entirety of each of which is incorporated herein by reference.

BACKGROUND

Veterinary hospitals provide many medical services during the course of caring for a patient. Pet insurance is one of these many services. Often, patients have health problems that require veterinary care above and beyond what a pet owner is prepared to pay out-of-pocket at the time services are provided, even when they have pet insurance coverage. The pet owner files a claim after leaving the veterinary practice and receives notice of coverage, eligibility and payment, if applicable, from the insurance company. These processes and systems are cumbersome and do not allow a pet owner to rapidly obtain or utilize pet medical insurance.

For the veterinary hospital, existing systems do not provide them with real-time, accurate information about the status of a pet's insurance policy, eligibility of coverage, status of a claim, or facilitate the offering of pet insurance coverage. Most systems are not responsive enough to effectively aid a veterinary practice in managing their practice, frustrating the hospital and the pet owner with the delay.

Additionally, due to the delay in claims processing and the need for the pet owner to cover the expense of medical services at time of service and prior to being reimbursed by the insurance company, the hospital must often provide alternate courses of care that are less expensive, more affordable for pet owners. This is counter-intuitive to the purpose of pet medical insurance coverage.

Thus, it is desirable to provide a pet medical insurance system and method to overcome the above limitations and it is to this end that the disclosure is directed. It is also within the scope of the disclosure to facilitate medical coverage and services at veterinary hospitals outside of pet insurance, such as wellness plans, radiology and lab, and similar services provided at veterinary hospitals utilizing the same system and method implementation.

BRIEF DESCRIPTION OF THE DRAWINGS

The disclosure will be better understood if reference is made to the accompanying drawings, in which:

FIG. 3 illustrates an example of a user interface of the pet medical insurance system;

FIG. 5 illustrates an example of a user interface of appointment data and insurance interaction;

FIG. 7 illustrates an example of a user interface for offering pet insurance coverage to a pet owner;

FIGS. 8A and 8B illustrate an example of a user interface for tracking insurance offers;

FIGS. 11A and 11B illustrate an example of a user interface for medical records requests;

FIGS. 12A and 12B illustrate an example of a user interface for completing medical records requests;

FIGS. 14A and 14B illustrate an example of a user interface for submitting claims in the pet insurance system;

FIG. 15 illustrates an example of a user interface indicating claims outcomes.

DETAILED DESCRIPTION OF ONE OR MORE EMBODIMENTS

The disclosure is particularly applicable to a cloud computing architecture pet insurance system and it is in this context that the disclosure will be described. It will be appreciated, however, that the system and method has greater utility.

In the disclosure set forth below, a pet owner is a guardian of the pet and could be the pet owner, pet sitter, or similar pet guardian. In the disclosure set forth below, a patient refers to an animal being treated by a veterinary practice. A patient also may be referred to as "pet". In the disclosure below, a veterinary practice refers to a hospital, clinic or similar where services are provided for an animal.

Figure 1:
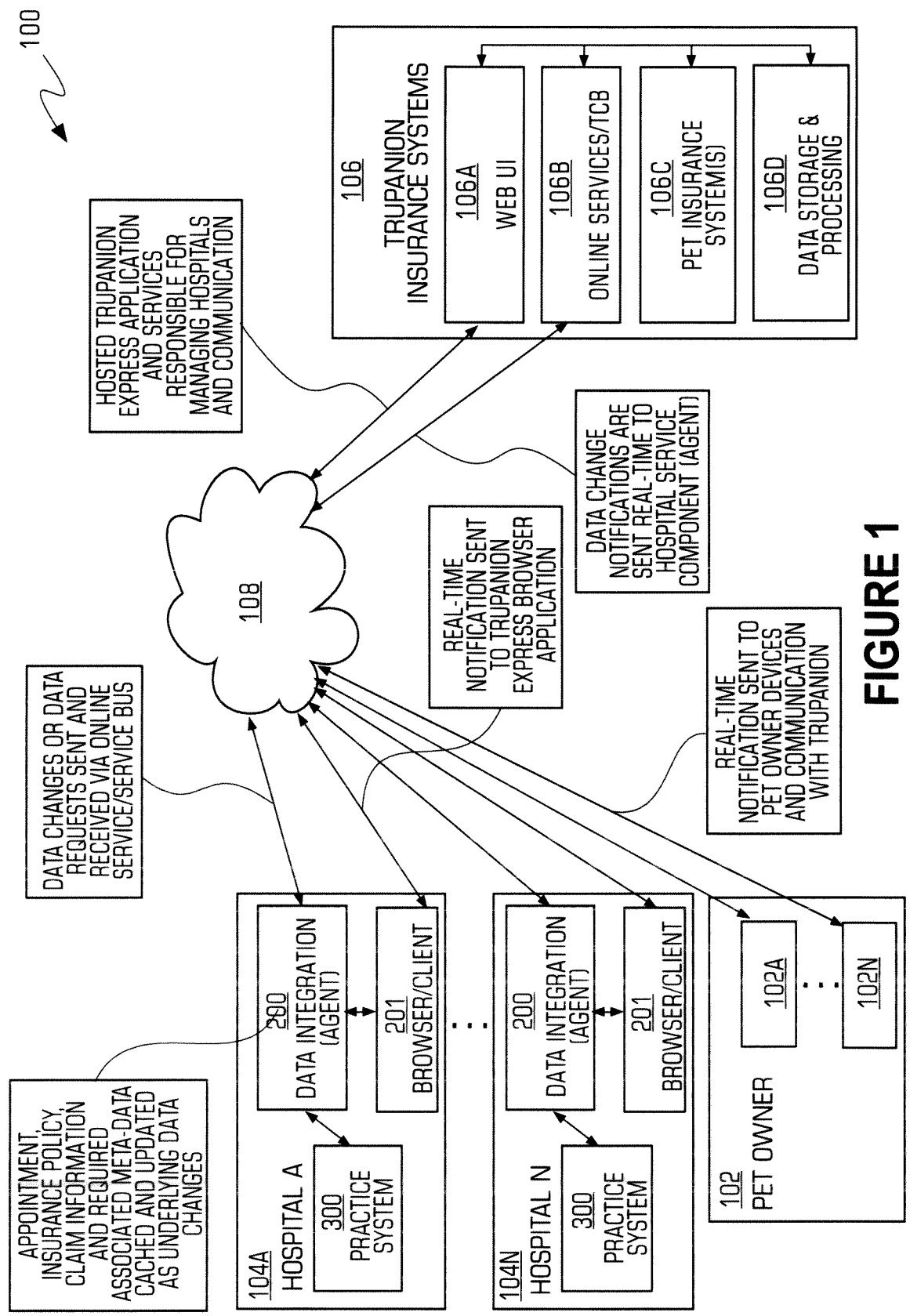
FIG. 1 is a diagram of an implementation of a pet medical insurance system.

FIG. 1 is a diagram of an implementation of pet insurance system 100. The implementation in FIG. 1 is cloud computing architecture. However, the system may be implemented in a client/server architecture, a mainframe architecture, a software as a service model and the like, all of which are within the scope of this disclosure. The system may include one or more computing devices 102, and each computing device may be used by a pet owner to connect to and interact with the pet insurance backend component 106 over a communication path 108. The system may also have one or more computing devices 104 such as 104A, . . . , 104N and each computing device may be used by (or integrated into) a veterinary practice and allow the veterinary practice to interact with a pet insurance backend component 106 or the communications path 108. Each computing device 102, 104 may be a processor based device with storage, memory, a display and wireless or wired connectivity circuits that allow the computing device 102, 104 to interact with the backend component 106. For example, each computing device may be a smartphone device, such as a device operating using the iOS, Android or Symbian operating systems, a personal computer, a client/server system, a terminal, a tablet computer, a cellular phone and any other device that would be capable of interacting with the backend component 106. In one implementation, each of the computing device 104 may have a data integration agent 200 and a client 201 that interacts with the backend component 106. In one implementation, the data integration agent 200 and the client 201 may be a plurality of lines of code executed by the processor of the computing device. In one implementation, each of the computing devices 102, 104 may have a browser that interacts with the backend component 106 displays web pages and allows the user to enter information into forms. In one implementation, the browser may be a plurality of lines of computer code executed by the processor of the computing device 102, 104.

The communication path 108 may be a wired or wireless network that may be unsecure or secure and uses typical protocols for the exchange of data between the computing devices 102, 104 and the backend component 106 For example, the communication path 108 may be an Ethernet network, the Internet, a wireless cellular network, a wireless digital data network and the like or any combination thereof and the system is not limited to any particular communication path 108. In the implementation in which the communication path 108 is the Internet, the communication path 108 may use the known HTTP or HTTPS protocol for data communications.

The backend component 106 may be implemented as one or more computing resources or hardware devices. In one implementation, the backend component 106 may be one or more server computers, one or more cloud computing resources and the like and each resource has one or more processors, memory, persistent storage and the like. The backend component 106 may further comprise a web server 106A online services 106B, a pet insurance management component 106C and data storage and processing 106D that are coupled together as shown in FIG. 1. The web server 106A that may be implemented as a hardware web server or a software implemented web server, may generate and exchange web pages with each computing device 102, 104 that is using a browser. The online services—Trupanion Central Services, or TCS—106B, may be implemented as a plurality of lines of computer code and may generate or exchange information with computing devices 102, 104 directly or through communication path 108 utilizing SignalR, ServiceBus, or similar notification services. The pet insurance management component 106B may be implemented as a plurality of lines of computer code that are stored in the computing resources and then executed by the processor(s) of the computing resources to implement the pet insurance management functions that are described below in more detail. The data processing and storage device 106D may be a hardware storage device or a software implemented storage device, such as a database, that stores user and veterinary practice information for the system, stores information about each insurance offer, stores information about each pet that is enrolled in the pet insurance system, and stores the information about each pet insurance claim in the system.

The communications path 108 can enable exchange of data between different programmatic elements running on the computing devices 102, 104 and different programmatic elements running on the backend server. For example, in each veterinary practice, the respective computing device 104A . . . 104N can comprise a respective data integration agent 200 and browser 201, each of which can independently communicate data using the communication path 108. The communication path enables communication with a plurality of programmatic elements in the backend component 106, including a web server 106A and online services 106B. The web server 106A can include a web user interface configured to exchange information between the computing devices 104A . . . 104N of the respective veterinary practices and the backend component 106. Each of the computing devices 104A . . . 104N can receive information from users in a practice information management system 300 and communicate with the respective data integration agent 200 of the computing device. The data integration agent thus provides a connection between the user information provided to the practice information management system 300 and the backend component 106 via the communications path 108.

As the data integration agent 200 receives information from the practice information management system 300, the data integration agent 200 caches relevant data such as appointment information, insurance policy claim information, and required associated meta-data. This cached information can be updated as the underlying data is changed. When the data changes, the data integration agent 200 can transmit information indicating the data change to the backend component 106. The backend component can transmit data change notifications in real time to the respective computing devices 104A . . . 104N, thereby informing the devices of data changes in real time. The data change notifications can be sent to an express browser application operating on the computing devices 104A . . . 104N. The user device 102 of pet owners can also receive real-time notifications via a web browser interface, allowing the user device to receive data updates in real time as the user device communicates with the backend 106 via the communications path 108.

Figure 2:
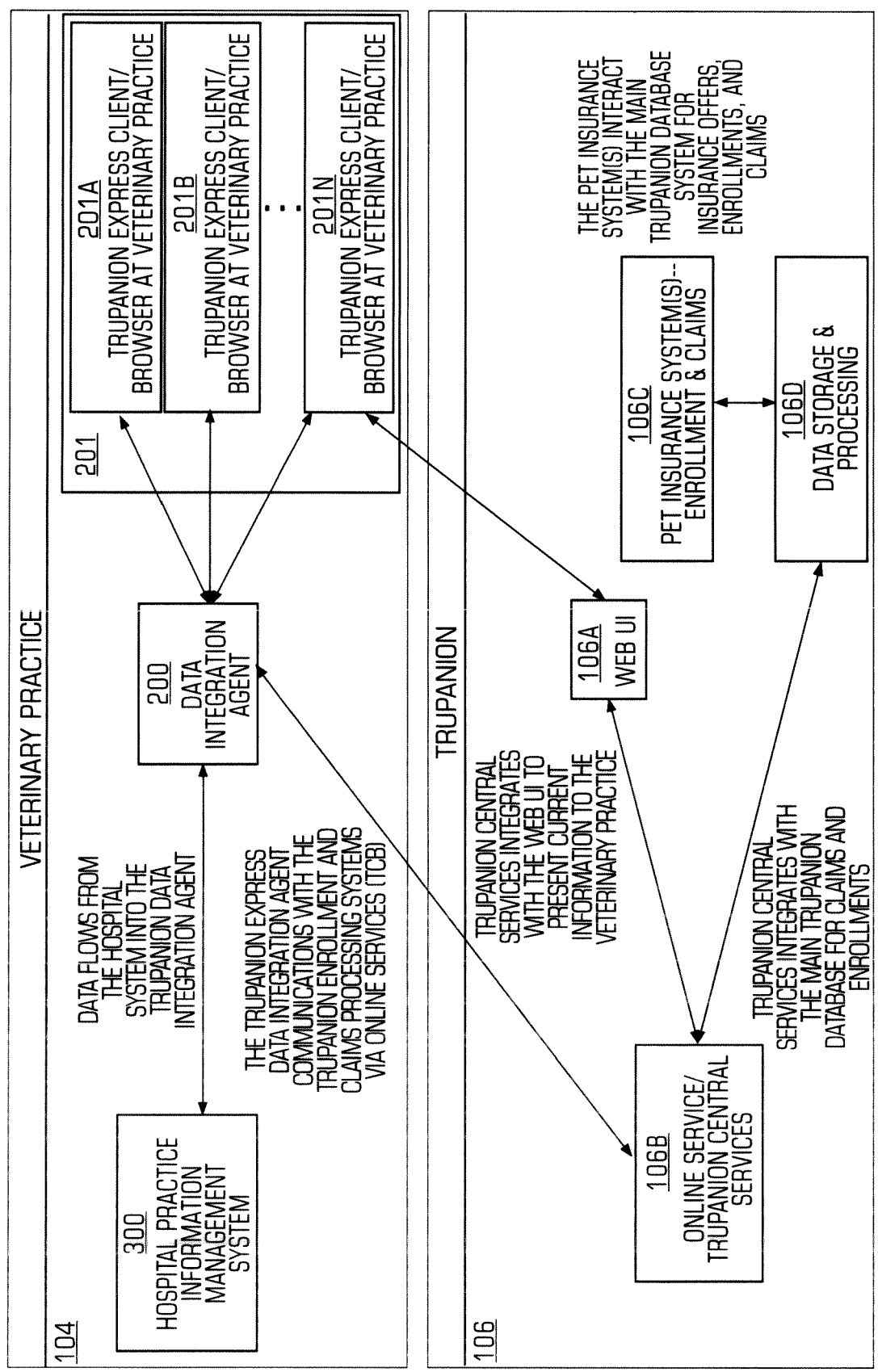
FIG. 2 illustrates more details of the pet medical insurance system.

FIG. 2 illustrates more details of the pet insurance system and in particular the components in each veterinary practice computing device 104 and the backend component 106 and the interactions between the two. As shown the veterinary practice may have one or more browsers/clients 201, a hospital practice information management system 300, and a data integration agent 200. As shown, data from the hospital practice information management system 300 flows into the data integration agent 200 and the data integration agent 200 connects to and communicates with the backend component 106. Online services 106B of the backend component 106 receives the communications from the data integration agent 200, and communicates with the data integration agent 200 as well as the web user interface 106A and a database 106D for data storage and processing. The database 106D is managed using a database system that allows for interactions with a pet insurance system 106C to handle features such as insurance offers, enrollments, and claims. The data integration agent 200 also connects to and communicates with one or more client/browsers 201 in the computing devices 104. In one implementation, each of the components of the veterinary practice computing device 104 may be a plurality of lines of computer code that are executed by a processor of the computing device 104. The Hospital Practice Information Management System (PIMS) is an existing system used by a veterinary practice that use database and visualization technologies (user interface) with the aim to support various hospital/patient management and administration tasks. Different PIMS manufacturers include different modules that allow for many common hospital technology requirements that may include inventory tracking, procedure codes, connection to diagnostic equipment and service providers, connection to a variety of radiology modalities and services, and invoice generation.

The data integration agent 200 may be provided by the pet insurance backend system 106 and may be installed in the computing device 104 of the veterinary practice. The data integration agent 200 is a system which integrates with these varied systems to provide added value and operational simplicity for employees of the veterinary practice and pet owners. The data integration agent is responsible for retrieving and mapping data from the PIMS 300, sending communications to and receiving information from Trupanion Central Services 106B about claim, insurance offers, and enrollments, and communication with the Trupanion Express clients/browsers 201. The data integration agent 200 employs various technological mechanisms to limit traffic between Trupanion Central Services 106B and Trupanion Express clients/browsers 201, as well as the PIMS 300, creating efficient correspondence between all systems. The data integration agent 200 may include an abstracted engine that allows communication with various PIMS systems on the market today, as well as the ability to integrate with additional in the future in a plug-and-play fashion.

The client/browser 200, is the user interface for Trupanion Express. It communicates with the data integration agent 200 and the web UI 106A with the aim to exchange information between the hospital and the backend component 106. Integrating services provided by the backend system 106 via the web user interface 106A allows the system to provide veterinary practices with current, real-time access to information stored in the backend system 106. The client/browser allows submitting claims, issuing insurance offers, searching PIMS data for clients, appointments, mapping clients between systems, and displaying all of the information for these activities in a digestible way for veterinary practice employees—resulting in improved patient care.

The backend component 106 may further comprise a services component 106B, that may be known as Trupanion Central Services, a data storage and processing component 106D, and a pet insurance system(s) 106C, that may be comprised of enrollment and claims systems that are coupled together as shown in FIG. 2. Sample data is included in the below table:

| Sample Data Exchanged Between the Veterinary Practice & Trupanion | Enrollment Sample Data | Claims Sample Data |
| --- | --- | --- |
| Patient demographics | Policy ID & type | Claims basics |
| Client demographics | Policy status | Claiming veterinary practice information |
| Claim form information | Enrollment veterinary practice information | Claim outcomes & amount covered |
| Invoices/estimates | Policy coverage details | Claims payments |
| Medical record information | | |
| Insurance offer information | | |

In one implementation, each of the components of the backend 106 may be a plurality of lines of computer code that are executed by a processor of the computing device 106. The services component 106B integrates with data storage and processing 106D. The enrollment processing system and claims processing system—pet insurance systems 106C—may interact with the data storage and processing systems 106D allowing insurance offers to be issued and activated and claims to be processed. The services component 106B is a service inside Trupanion's network and processes requests from and sends information to the data integration agent 200 and passes appropriately formed requests to the data storage & processing systems 106D. The data storage and processing system 106D is any location where transactional data for Trupanion's various IT systems is processed and/or stored. The pet insurance system 106C is comprised of the enrollment processing system, the system that issues insurance offers to pet owners, and the claims processing system, the system that catalogs the collection of medical records that enables claims adjudicators to manage and process pet owner claims. The pet insurance system 100 is revolutionary in that it enables claims to be adjudicated very quickly—allowing the pet owner to not pay out-of-pocket expenses at the veterinary practice. Said another way, the pet insurance system 100 allows Trupanion to pay the veterinary hospital directly with the invoice while the customer is waiting to checkout, similar to the concept of "co-pay" in human health care. The pet insurance system 100 allows for near real-time claims submission and claims processing, enabling claim adjudication at point-of-sale at the veterinary practice. A typical system uses typical channels such as fax or mail that support a delayed reimbursement model for veterinary practices and/or pet owners.

FIG. 3 illustrates an example of a user interface 500 of the pet insurance system. The user interface may include a navigation portion 501 that allows the user to navigate around to various parts of the pet insurance system user interface. The user interface may include a status 502 for each pet to indicate the current coverage of that pet. The user interface may further include an action button 503 allowing the user to submit claims or issue an insurance offer to a selected pet. The user interface may have status indicators for current claims transactions 504. The user interface may also have status indicators for current offers of insurance 505.

Figure 4:
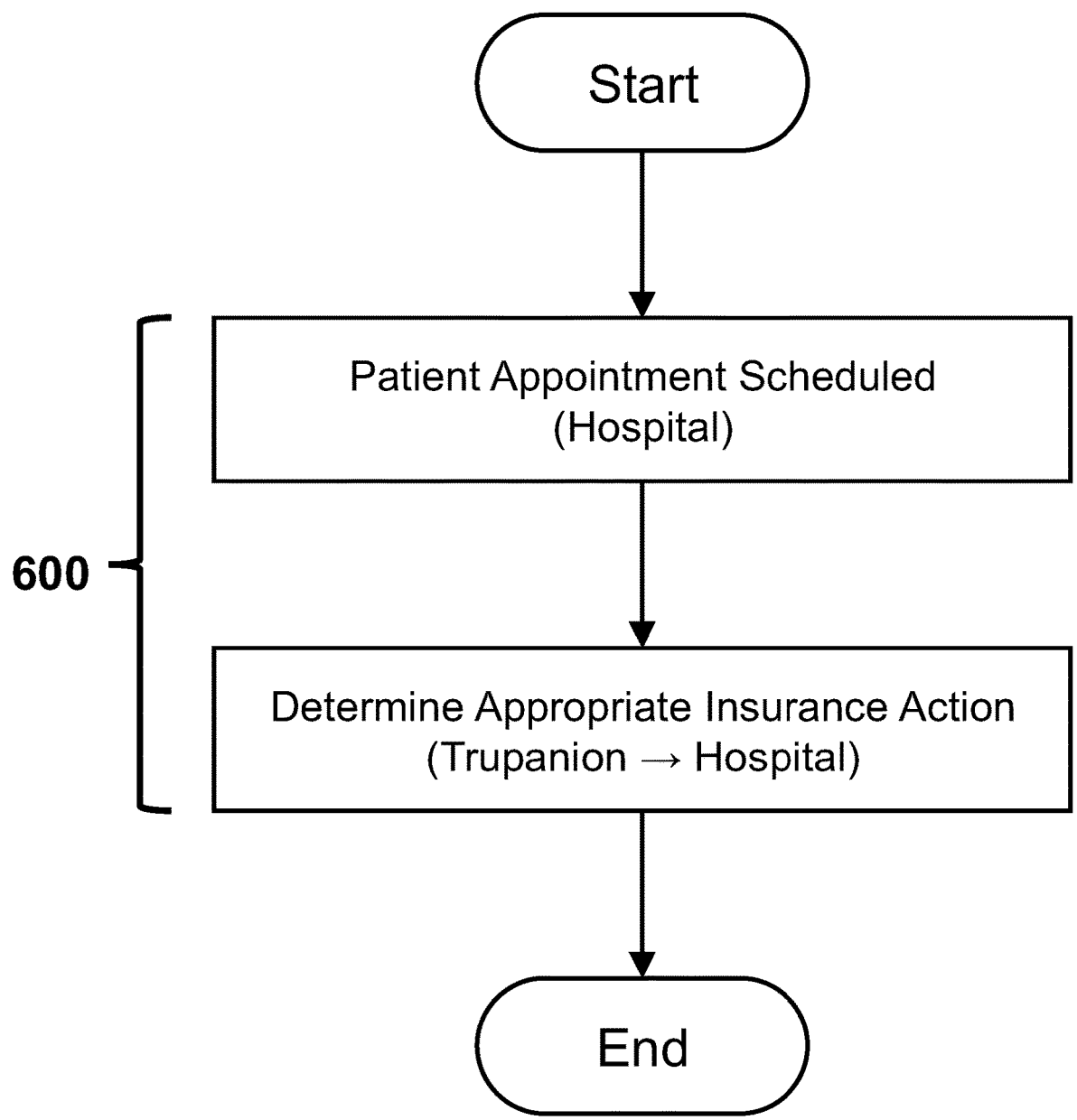
FIG. 4 illustrates a method of interacting with hospital appointment information and providing insurance action options.
Figure 5:
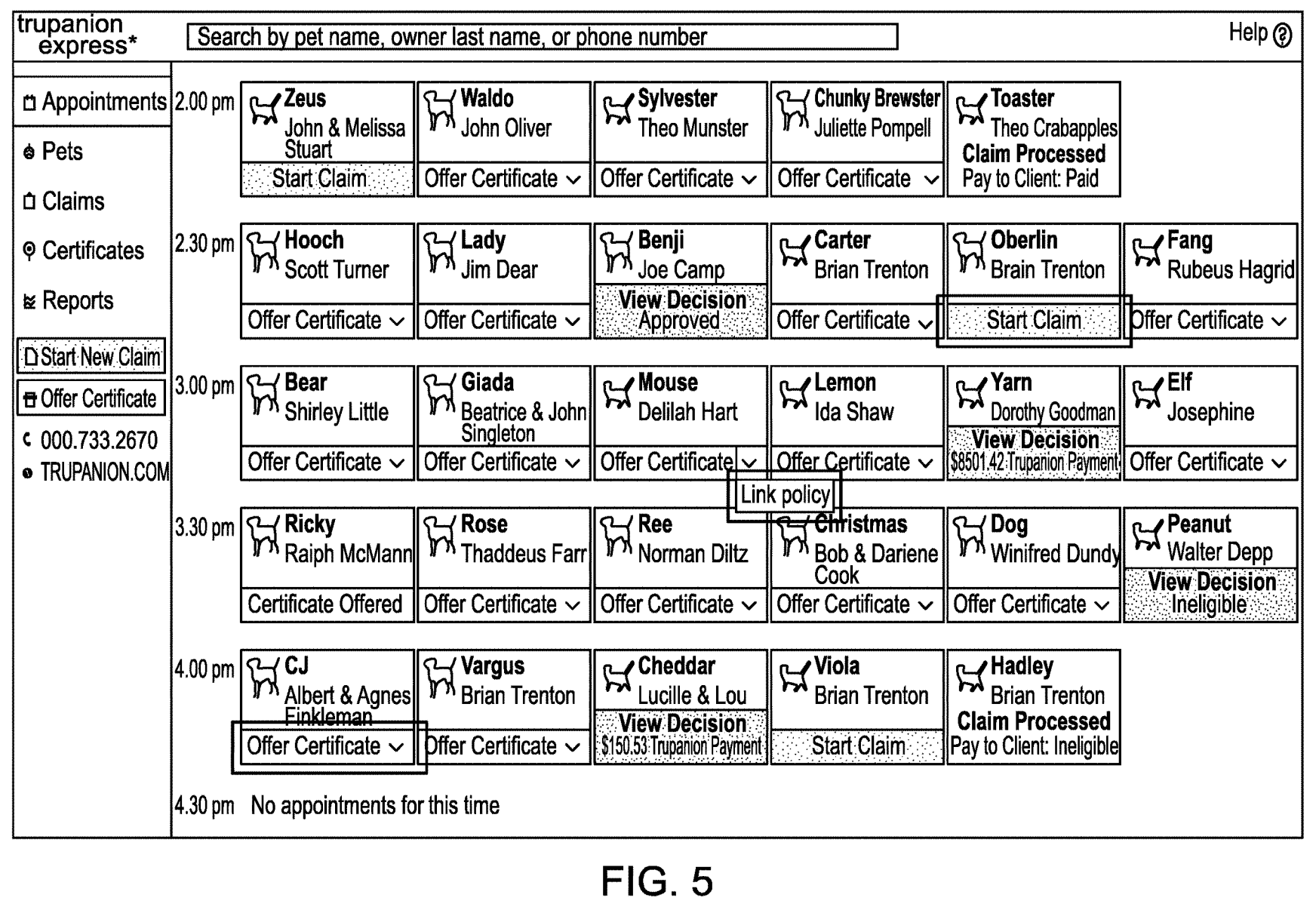

FIG. 4 illustrates a method 600 for determining the current pet insurance coverage for patient with scheduled appointments in the hospital practice information management system 300 and displaying the appropriate action in the pet insurance system user interface 500. FIG. 5 illustrates an example of a user interface displaying the appropriate insurance based on the method illustrated in FIG. 4.

Figure 6:
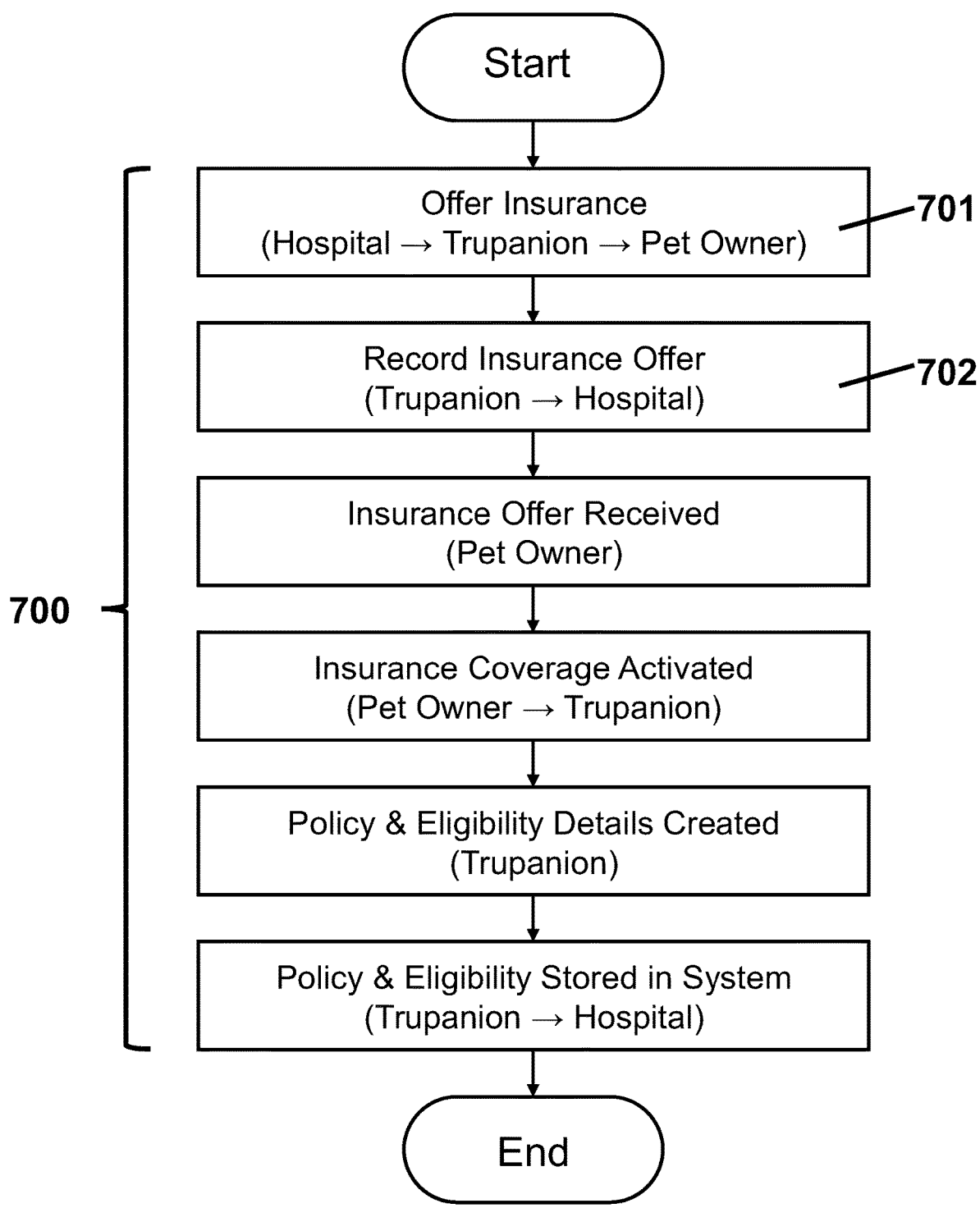
FIG. 6 illustrates a method for offering insurance, tracking insurance offers, and providing insurance coverage and eligibility details.
Figure 7:
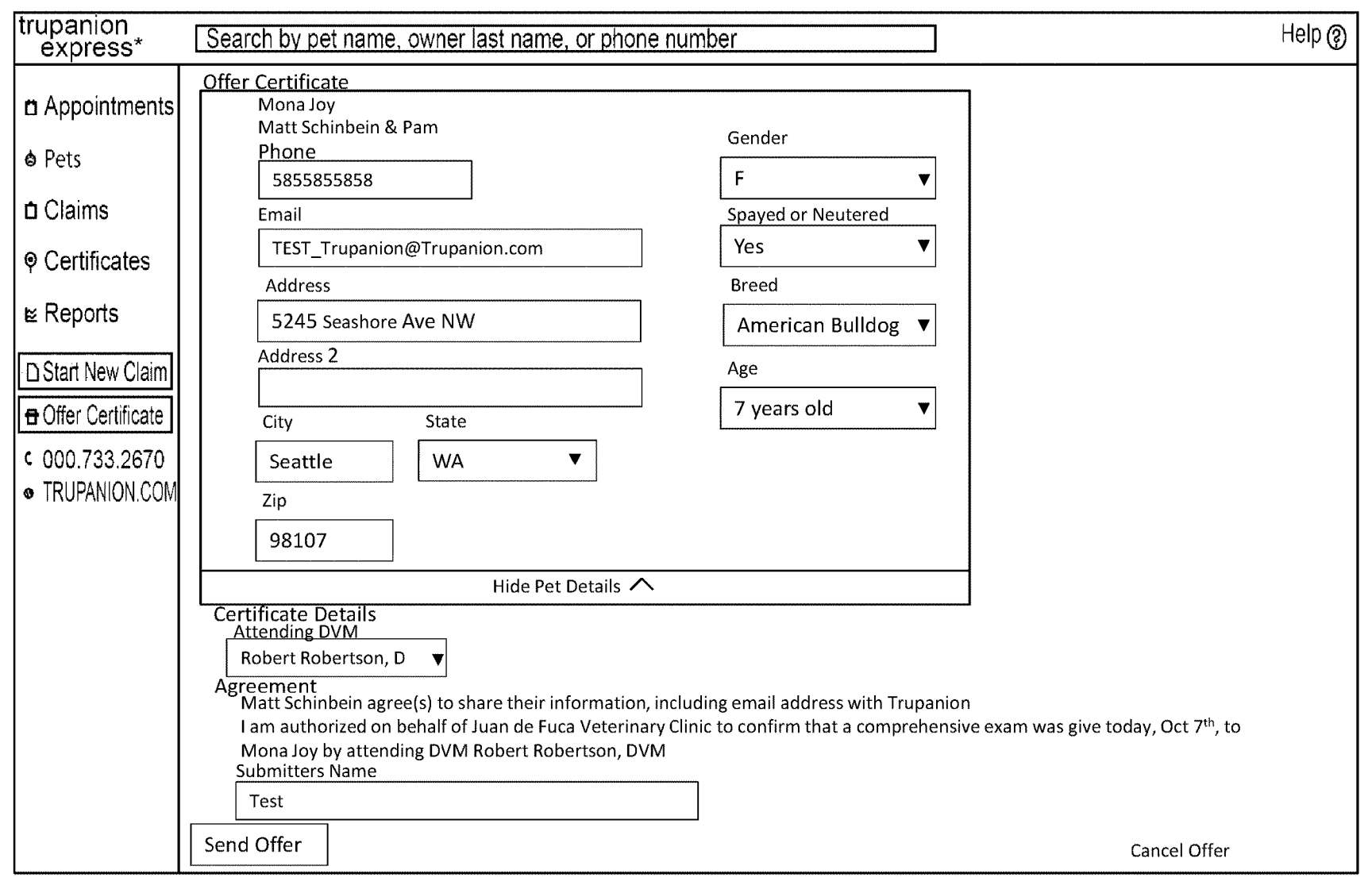

FIG. 6 illustrates a method 700 for obtaining insurance and tracking insurance offers using the pet insurance system and FIG. 7 illustrates an example of a user interface for offering pet insurance to a pet owner. The pet insurance system makes it easier for a pet owner to get pet insurance and then quickly be able to have proof of the pet insurance in the form of an insurance offer that can be presented to the veterinary practice to establish the insurance of the pet. In the method 700, a veterinary practice may provide a pet owner an insurance offer 701 which is recorded in Trupanion systems 702 through the data integration agent 200. When the veterinary practice offers the insurance to the pet owner, an employee of the veterinary practice may enter the insurance offer into the client 201, such as shown in FIG. 7, and the information about the insurance offer is passed onto the backend component 106 through the data integration agent 200. The pet owner, using a computing device 102, can receive the insurance offer and may then activate the insurance offer, and obtain pet insurance, using an email link or by phone which is sent to the backend component 106. Once the pet owner activates the insurance coverage, policy and eligibility details are created and stored in the system, and the pet owner receives proof of insurance which is also passed back to the veterinary practice through the data integration component 200 so that the veterinary practice receives quick notice of the insurance for the pet. In addition, since the computing device 104 and the backend component 106 are integrated as shown in FIG. 2, all parties involved are rapidly notified of changes to the pet's insurance coverage. For example, this means the veterinary practice can be comfortable that the pet has insurance for the procedure that is about to be performed. The system may also display the treatment or procedure that is, has been or will be performed on a particular patient or by a particular employee at the veterinary practice.

Figure 8A:
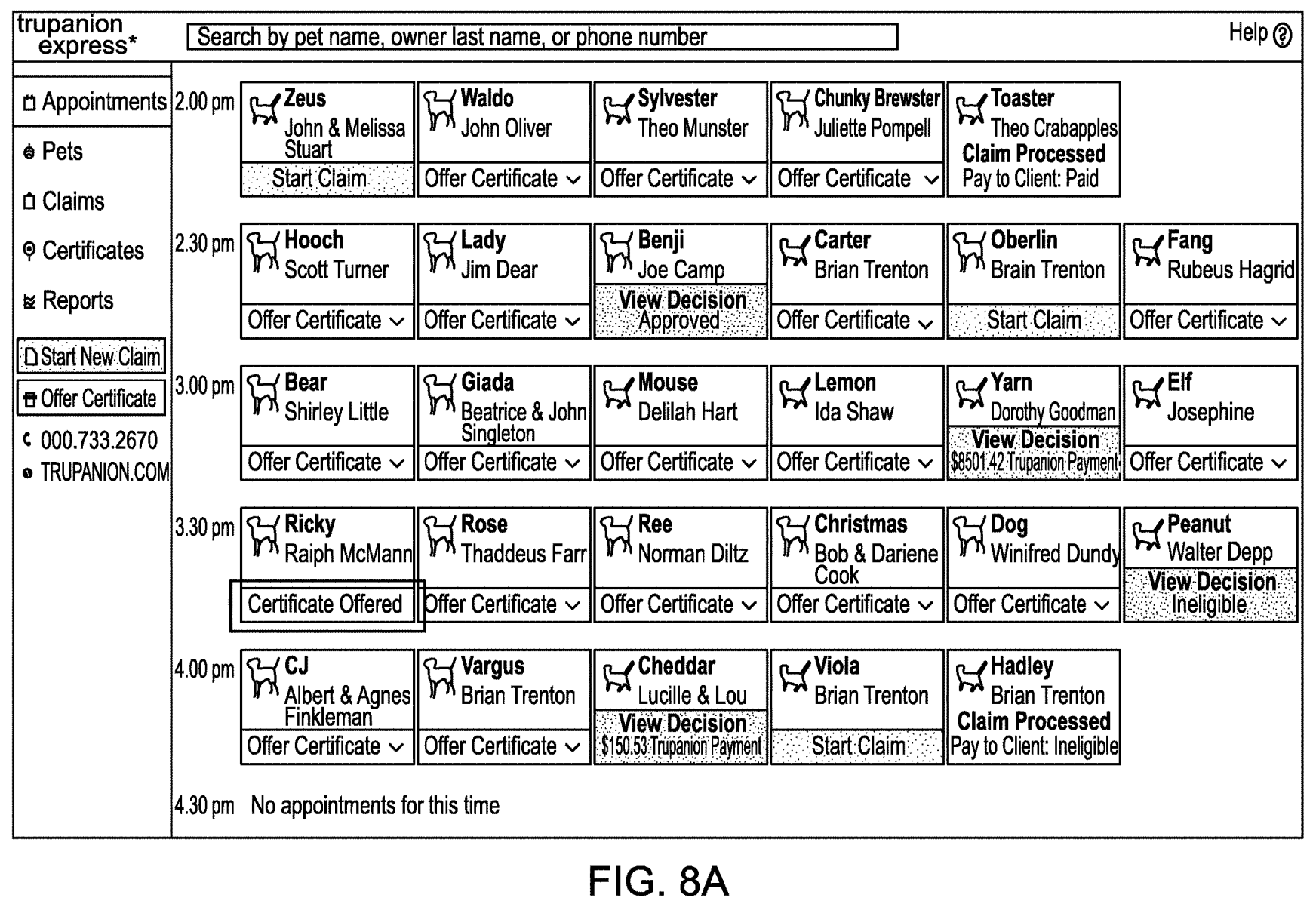
Figure 9:
FIG. 9 illustrates an example of a user interface displaying the status of a particular pet's medical insurance coverage and eligibility.

FIGS. 8A and 8B illustrate examples of a user interface for tracking pet insurance offers through the pet insurance system user interface in the client/browser 201 in the veterinary practice. FIG. 9 illustrates an example of a user interface of a particular pet's insurance coverage eligibility once the insurance offer has been activated.

Figure 10:
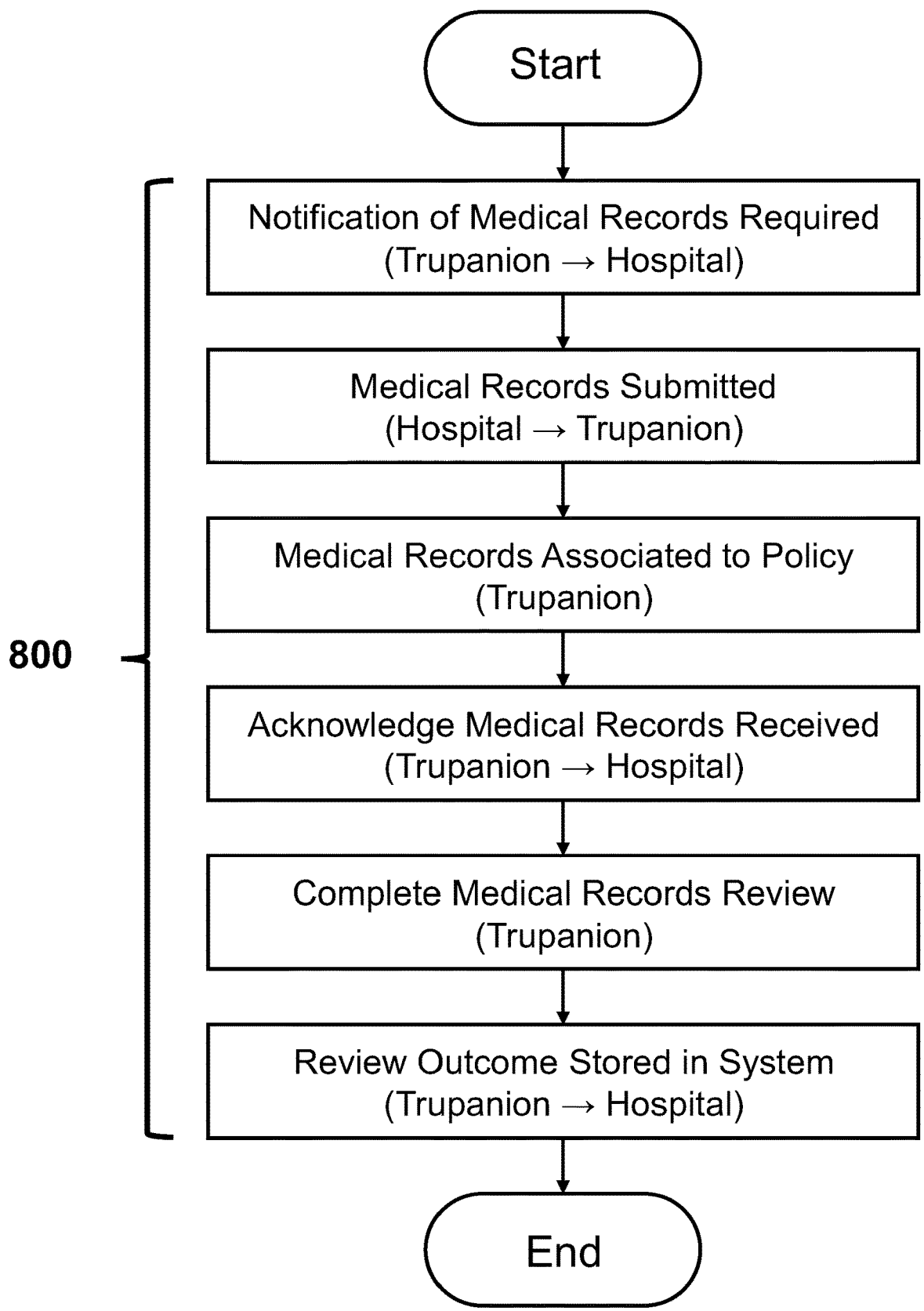
FIG. 10 illustrates a method for requesting and receiving medical record information.
Figure 11A:
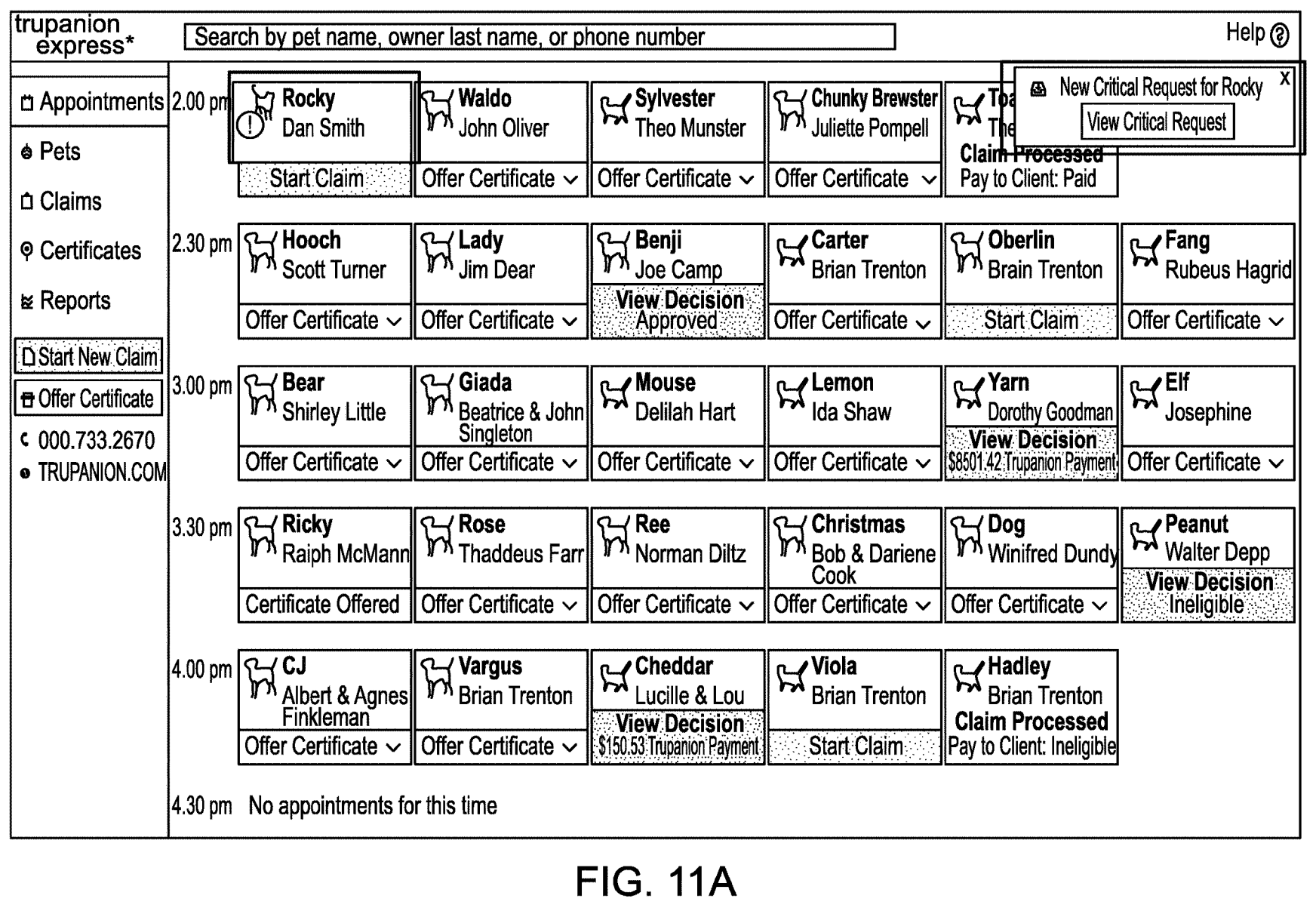
Figure 12A:
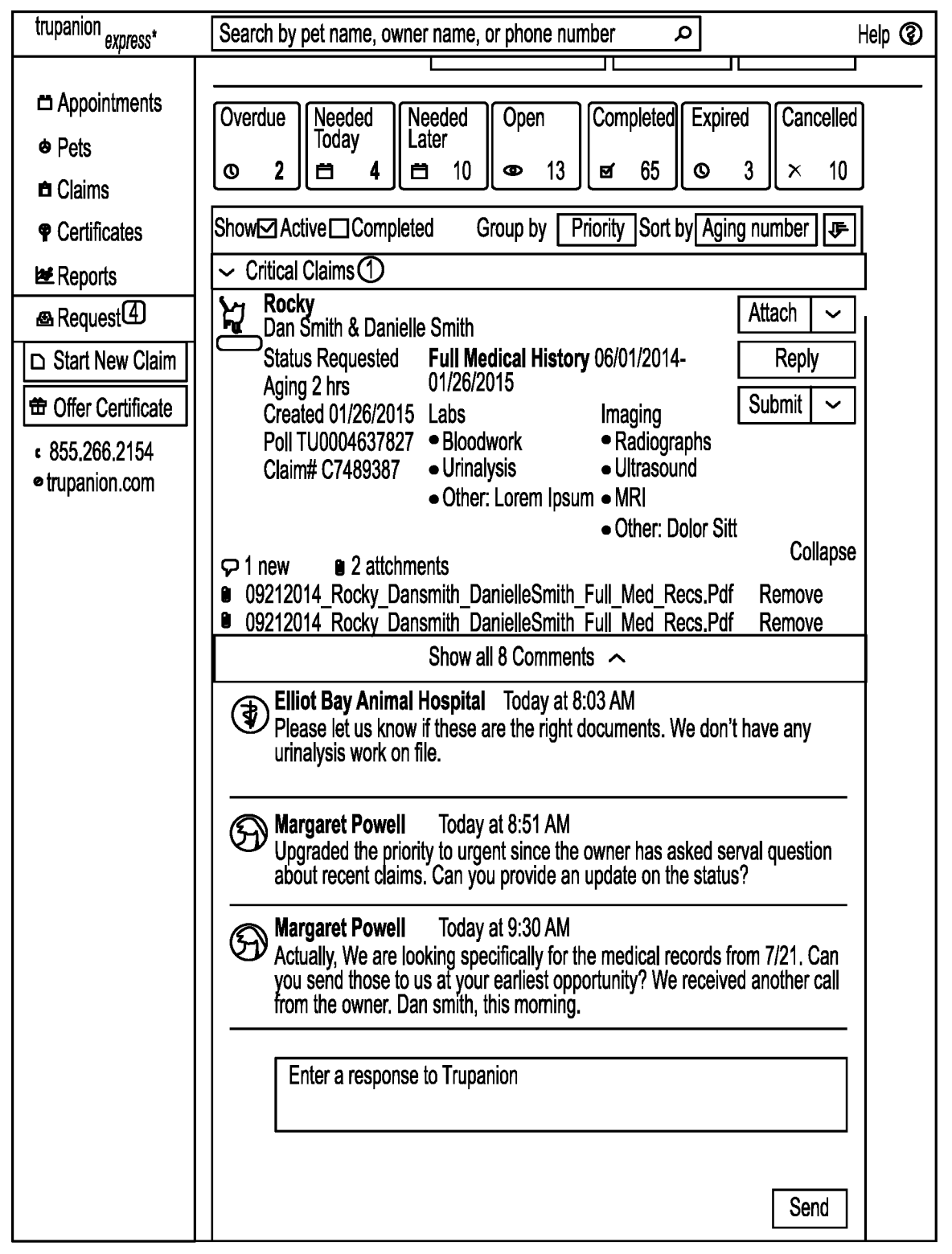
Figure 12B:
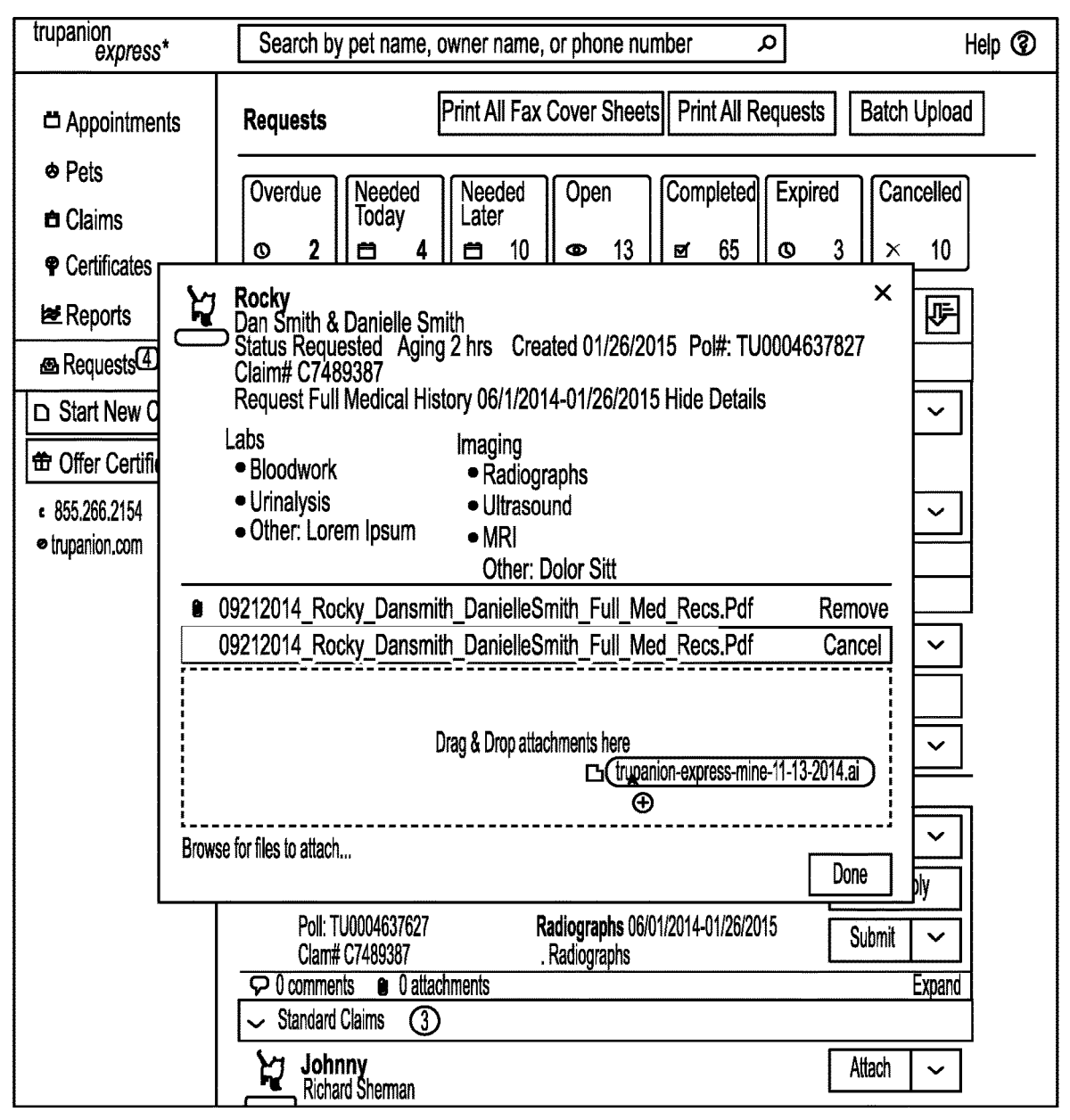

FIG. 10 illustrates a method 800 for requesting and receiving medical record information used to determine a pet's eligibility for insurance coverage. When the pet insurance system is generating the eligibility the computing device 200 and the pet insurance systems 106C may obtain a history of a pet from any veterinary practice that has seen the pet in the past through the data integration component 200. The pet insurance components 106C may then structure that data and generate an eligibility of coverage. The system may then display that eligibility of coverage to the users of the system which allows all of the users to rapidly see the coverage status for a pet in a user interface (refer to FIG. 9). During the course of collecting medical record information for a pet, it may be required for a hospital to respond directly to requests for information utilizing the user interface of the pet insurance system. FIGS. 11A and 11B illustrate an example of a user interface for notification of a request for medical records and tracking of medical records requests. FIGS. 12A and 12B illustrate an example of a user interface for submitting requested records and completing medical records requests.

Figure 13:
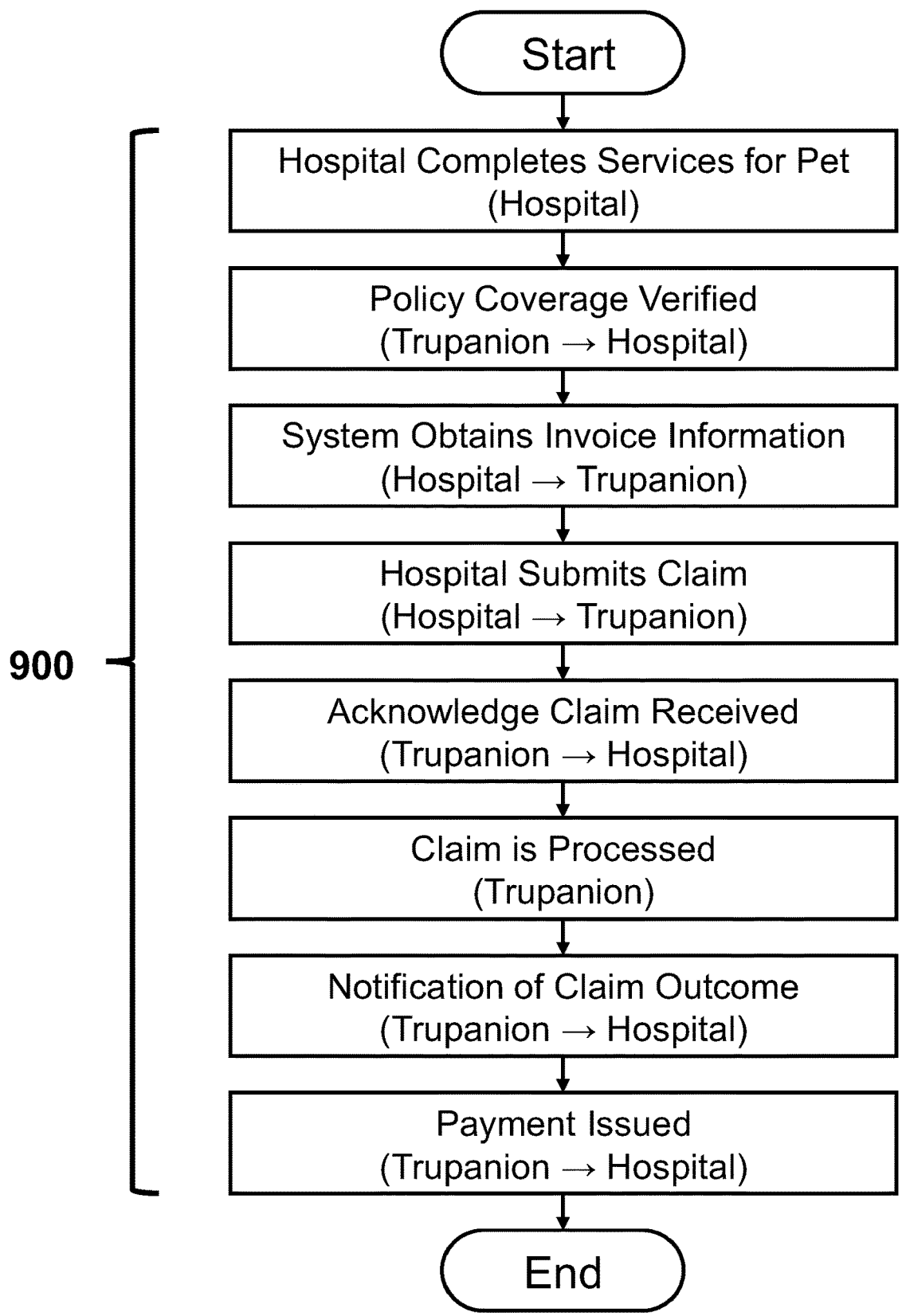
FIG. 13 illustrates a method for submitting and processing a claim in the pet insurance system.
Figure 14B:
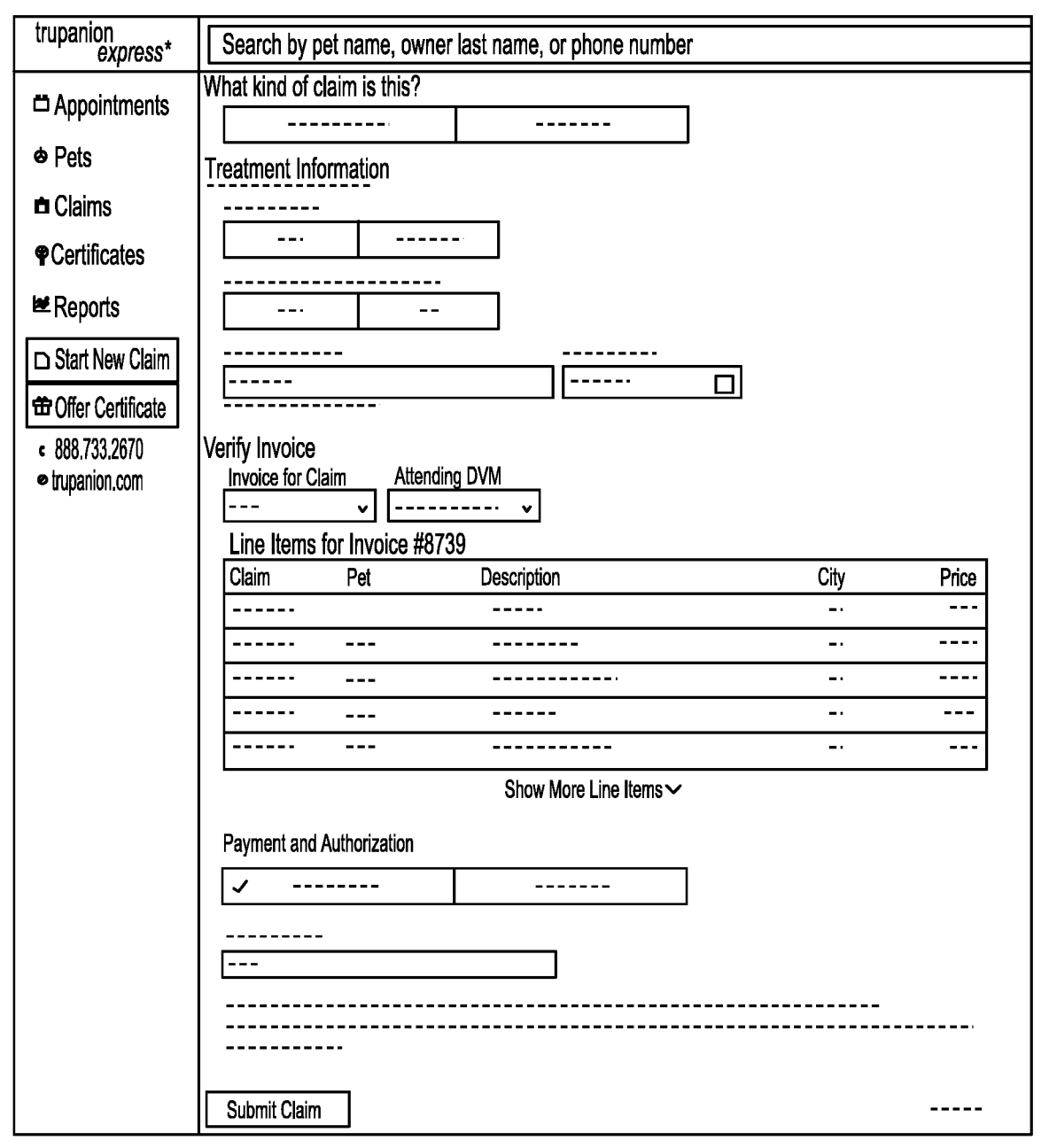

FIG. 13 illustrates a method 900 for submitting and processing a claim in the pet insurance system. Since the backend component and each computing device in the veterinary practice are integrated, as seen in FIG. 2, and the system has determined a patient's eligible coverage, an insurance claim may be quickly processed by the claims processing component of the pet insurance component 106C. A claim starts when an employee or doctor of a veterinary hospital completes services for a pet. The policy coverage can be verified by the data integration agent 200, which can indicate the verification to the veterinary practice. The system can obtain invoice information from the veterinary practice, which may be sent to the data integration agent 200. The veterinary practice submits a claim (see FIG. 14A for an example) for the treatment using a claim form (such as shown in FIG. 14B) that is generated by the client/browser 201 in combination with the data integration agent 200. The receipt of the claim by the data integration agent 200 can be acknowledged to the veterinary practice. The pet insurance company, through the pet insurance systems 106C, may then process the claim. The pet insurance company has the status of the pet's eligibility for coverage and this is able to quickly approve or deny the insurance claim for the pet. If the claim is approved, the claim may be paid directly to the veterinary practice (in one implementation, electronically via ACH) and then the pet owner pays their portion to the veterinary practice. In this manner the system allows a claim to be quickly processed and then paid if the insurance claim is approved.

FIG. 15 is an example of a user interface of pet insurance system 100 highlighting display of communication from Trupanion to the veterinary practice claim outcome information.

Figure 16:
FIG. 16 illustrates an example of a user interface for claims submission and payment tracking.

FIG. 16 is an example of a user interface for pet insurance system 100 for tracking of the status of claims submitted and the outcomes and payments for those claims.

While the foregoing has been with reference to a particular embodiment of the invention, it will be appreciated by those skilled in the art that changes in this embodiment may be made without departing from the principles and spirit of the disclosure, the scope of which is defined by the appended claims.

The invention claimed is:

1. A pet medical insurance system comprising:
a backend component implemented by a computer, wherein the backend component comprises a services component configured to be in communication with a plurality of practice management systems and a network of devices over a computer network; and
a plurality of data integration systems each is implemented by a computing device integrated into a respective practice management system in a veterinary practice,
wherein the plurality of data integration systems provide connection between different programmatic elements running on the backend component and various different practice management systems, and wherein each data integration system is configured to:
 (i) cache, in a memory storage in the respective practice management system, relevant data from a set of underlying data in an existing database of the respective practice management system, wherein the relevant data includes data from the set of underlying data that is about a treatment or procedure associated with a patient and the associated meta-data that is required for determining an insurance coverage associated with the patient,
 (ii) determine a change to the set of underlying data in the respective practice management system, and upon detection of the change to the relevant data, automatically cache the updated relevant data in the memory storage in the respective practice management system,
 (iii) automatically transmit an indication of the change and the cached updated relevant data in the respective practice management system to the backend component, thereby limiting the traffic between the respective practice management system and the backend component,
wherein the backend component is configured to:
 (i) receive the indication of the change to the relevant data of the respective practice management system and the cached updated relevant data from of the respective practice management system;
 (ii) automatically generate a notification indicative of the change to the relevant data of the respective practice management system and the cached set of updated relevant data of the respective practice management system;
 (iii) transmit, over the computer network, the notification indicative of the change to the set of relevant data of the respective practice management system and the cached set of updated relevant data of the respective practice management system to the network of devices and the plurality of practice management systems in real-time; and (iv) generate a user interface rendered on a display of the network of devices and the plurality of practice management system of a respective veterinary practice, and wherein upon receiving the notification or the cached updated relevant data the user interface is configured to:
display at least the notification or patient information related to the change in the relevant data within the user interface, so that the network of devices and the plurality of practice management systems have immediate access to up-to-date insurance information.

2. The pet medical insurance system of claim 1, wherein the relevant data is cached by the respective data integration system in a local memory of the respective veterinary practice.

3. The pet medical insurance system of claim 1, wherein an updated insurance coverage eligibility is determined by the backend component based at least in part on i) the change to the cached relevant data and ii) the cached updated relevant data.

4. The pet medical insurance system of claim 3, wherein the cached relevant data is transmitted from a database of the respective veterinary practice to the backend component via the respective data integration system.

5. The pet medical insurance system of claim 3, wherein the cached relevant data is transmitted from one or more databases of the plurality of veterinary practices that have stored a medical record of the patient.

6. The pet medical insurance system of claim 5, wherein the cached relevant data of the one or more other practice management systems is retrieved from the one or more databases by sending a request to the plurality of data integration agents integrated into the various different practice management systems.

7. The pet medical insurance system of claim 5, wherein the backend component is configured to structure the relevant data and generate an insurance coverage or the eligibility of insurance coverage associated with the patient.

8. The pet medical insurance system of claim 6, wherein the user interface is further configured to prompt a user to approve or deny the request for retrieving the relevant data associated with the patient.

9. The pet medical insurance system of claim 1, wherein the backend component further comprises a claim processing component that is configured to process a claim for one or more treatments and procedures for the patient.

10. The pet medical insurance system of claim 9, wherein the claim processing component is further configured to pay an amount to the respective veterinary practice after processing a claim.

11. The pet medical insurance system of claim 9, wherein the claim processing component is configured to process the claim for one or more treatments and procedures for the patient at the time of completion of the one or more treatments and procedures for the patient.

12. A pet medical insurance system for real-time claim processing, comprising:
a backend component implemented by a computer, wherein the backend component comprises a services component configured to be in communication with a plurality of practice management systems and a network of devices over a computer network; and
a plurality of data integration systems each integrated to a respective practice management system in a veterinary practice, wherein each data integration system is remote from the backend component and is implemented by a computing device integrated into the respective practice management system thereby allowing for data transmission between the backend component and the respective practice management system, and comprises an abstracted engine that interfaces with an existing database of the respective practice management system, and wherein the abstracted engine allows the plurality of data integration systems to communicate and process data across various different databases of the plurality of practice management systems;
wherein at least one of the plurality of data integration systems is implemented by a computing device integrated into a respective practice management system and is configured to:
(i) cache data in a memory storage in the respective practice management system, wherein the data includes relevant data related to information about a treatment or procedure associated with a patient and the associated meta-data that is required for determining an insurance coverage associated with the patient,
(ii) determine a change of a set of underlying data in an existing database of the respective practice management system, wherein the set of underlying data is selected according to the information in (i), and upon detection of the change, determine that the change of the set of underlying data changes the relevant data cached in the memory storage in the respective practice management system, and update the cached data and transmit information indicating the data change or the change in the relevant data to the backend component, thereby limiting the traffic through the backend component,
(iii) receive updated information related to an insurance associated with the patient from the backend component in substantially real-time;
wherein the backend component is configured to:
(i) receive the information indicating the data change or the change in relevant data from the at least one of the plurality of data integration systems;
(ii) automatically generate a notification indicative of the data change and updated information related to the insurance; and
(iii) transmit, over the computer network, the notification to the network of devices and the respective practice management system in the respective veterinary practice in substantially real-time, so that the network of devices and the plurality of practice management systems immediate access to up-to-date insurance information.

* * * * *